US008853168B2

(12) United States Patent
Stamler et al.

(10) Patent No.: US 8,853,168 B2
(45) Date of Patent: Oct. 7, 2014

(54) COMPOSITIONS FOR THE REVERSIBLE THIOESTERIFICATION OF SIGNALING PROTEINS AND METHODS OF USING SAME

(75) Inventors: Jonathan S. Stamler, Chapel Hill, NC (US); Jordan Gutterman, Houston, TX (US)

(73) Assignee: Duke University, Durham, NC (US)

( * ) Notice: Subject to any disclaimer, the term of this patent is extended or adjusted under 35 U.S.C. 154(b) by 630 days.

(21) Appl. No.: 11/488,992

(22) Filed: Jul. 18, 2006

(65) Prior Publication Data

US 2007/0066546 A1    Mar. 22, 2007

Related U.S. Application Data

(60) Provisional application No. 60/700,119, filed on Jul. 18, 2005.

(51) Int. Cl.
| | | |
|---|---|---|
| A61K 31/70 | (2006.01) | |
| A61K 38/00 | (2006.01) | |
| A61K 35/12 | (2006.01) | |
| C07H 17/04 | (2006.01) | |
| C12Q 1/26 | (2006.01) | |
| C12P 33/00 | (2006.01) | |
| C07K 1/113 | (2006.01) | |
| A61K 47/48 | (2006.01) | |
| G01N 33/50 | (2006.01) | |
| C07K 1/107 | (2006.01) | |
| C07H 15/24 | (2006.01) | |

(52) U.S. Cl.
CPC ........ *A61K 47/48246* (2013.01); *A61K 38/00* (2013.01); *C07K 1/1133* (2013.01); *G01N 33/5041* (2013.01); *G01N 33/5011* (2013.01); *A61K 47/48338* (2013.01); *C07K 1/1077* (2013.01); *C07H 15/24* (2013.01); *G01N 33/5023* (2013.01)
USPC .............. 514/23; 536/18.1; 435/25; 435/52; 435/252.3; 435/325; 435/366

(58) Field of Classification Search
CPC ....... A61K 31/70; A61K 38/00; A61K 35/12; C07H 17/04; C12Q 1/26; C12P 33/00
USPC ............. 514/23; 536/18.1; 435/25, 52, 252.3, 435/325, 366
See application file for complete search history.

(56) References Cited

U.S. PATENT DOCUMENTS 6,444,233 B1    9/2002   Arntzen et al.

FOREIGN PATENT DOCUMENTS

| CA | 2616589 A1 | 1/2007 |
| WO | 2007011985 A1 | 1/2007 |

OTHER PUBLICATIONS

Beutler et al. (1997), Bioorganic & Medicinal Chemistry, 5(8):1509-1517.
Brimecombe et al. (1999), Journal of Pharmacology and Experimental Therapeutics, 291:785-792.
Connolly (1983), Science, 221:709-713.
Dietrich et al. (2004), European Molecular Biology Organization, 5:1053-1057.
Dinkova-Kostova et al., (2002), Proc. Natl. Acad. Sci. USA, 99:11908-11913.
Francis et al. (2002), British Journal of Nutrition, 88(6):587-605.
Genschel (2004), Molecular Biology and Evolution, 21:1242-1251.
Gogarten et al. (2002), Annu. Rev. Microbiol., 56:263-287.
Haendeler et al. (2002), Nature Cell Biology, 4:743-749.
Hanausek et al. (2001), Proceedings of the National Academy of Sciences of the United States of America, 98(20):11551-11556.
Haridas et al. (2001), Proceedings of the National Academy of Sciences of the United States of America, 98(20):11557-11562.
Haridas et al. (2001), Proceedings of the National Academy of Sciences of the United States of America, 98(10):5821-5826.
Haridas et al. (2004), The Journal of Clinical Investigation, 113(1):65-73.
Haridas et al. (2005), Proceedings of the National Academy of Sciences of the United States of America, 102(29):10088-10093.
Hausladen (1996), Cell, 86:719-729.
Hess et al. (2005), Nature Reviews Molecular Cell Biology. 6:150-166.
International Preliminary Report, Application No. PCT/US2006/027970, Issue Date: Jan. 22, 2008.
Jayatilake et al. (2003), Journal of Natural Products, 66(6):779-783.
Kim et al. (2002), Cell 109:383-396.
Kiuchi et al. (1997), Chemical and Pharmaceutical Bulletin 1997 Japan, 45(5):807-812.
Kratzke et al. (1992), The Journal of Biological Chemistry, 267:25998-26003.
Mannello et al. (2005), Current Cancer Drug Targets, 5:285-298.
Menon (Sarita) et al. (2003), Cancer Research, 63:2109-2117.
Okamoto et al. (2004), Biological Chemistry, 385:997-1006.
Rarey et al. (1996) Journal Molecular Biology, 261: 470-489.
Talalay et al. (2001), The Journal of Nutrition, 131: 3027S-3033S.
Tezuka et al. (2000), Journal of Natural Products, 63(12):1658-1664.
Vilela et al. (1993), Plantes Medicinales et Phytotherapie, 26(2):101-108.

(Continued)

*Primary Examiner* — Raymond Henley, III
(74) *Attorney, Agent, or Firm* — Ivor Elrifi; Matthew Pavao; Cooley LLP

(57) ABSTRACT

Avicins and other thioesterification agents are used to modify cysteine groups of signaling proteins in order to modify their activity. Pathologies associated with signaling proteins which are regulatable through this method are treated using these thioesterification agents. These pathologies include those involving proteins which modulate physiologic redox status of organisms including arthersclerosis, cancer, bacterial infection, inflammation, and neurological disorders.

27 Claims, 4 Drawing Sheets

(56) References Cited

OTHER PUBLICATIONS

Wakabayashi et al. (2004), Proc. Natl. Acad. Sci. USA, 101:2040-2045.
Yamawaki et al. (2005), The Journal of Clinical Investigation, 115:733-738.
Yoshikawa et al. (1997), Journal of Natural Products, 60(12)1269-1274.
Zhang et al. (1996), Journal of Natural Products, 62(6):877-881.
Zhang et al. (1999), Chemical & Pharmaceutical Bulletin, 47(3):388-393.
Zhang et al. (1999), Journal of Natural Products, 62(5):740-745.
Zhong Lei et al. (2003), Planta Medica, 69(6):561-563.

COMPOSITIONS FOR THE REVERSIBLE THIOESTERIFICATION OF SIGNALING PROTEINS AND METHODS OF USING SAME

RELATED APPLICATIONS

This application claims priority to U.S. Provisional Application No. 60/700,119, filed Jul. 18, 2005, the entire content of which is incorporated herein by reference.

FIELD OF THE INVENTION

The present invention provides small molecules analogs thereof and methods of using them for modulation of the action of signaling proteins by thioesterification and treatment of a pathology associated with the modulation of the action of signaling proteins by thioesterification.

BACKGROUND OF THE INVENTION

Thioesters are known to form in a variety of metabolic processes including fatty acid oxidation (Genschel, U. (2004) *Mol. Biol. Evol.* 21, 1242-1251), protein splicing (Gogarten, J. P., et al. (2002) *Annu. Rev. Microbiol.* 56, 263-287), and activation of enzyme intermediates (e.g., ligases). Cys thiols within numerous mammalian proteins are also posttranslationally modified by long-chain fatty acid (predominantly palmitate), which is added enzymatically via thioester→thioester transesterification from an activated acylCoA donor, and which is thought to play a role predominantly in subcellular localization (Dietrich, L. E. & Ungermann, C. (2004) *EMBO Rep.* 5, 1053-1057).

A variety of plant constituents, many of which are abundant in the diet, contain α,β-unsaturated carbonyl groups (Michael acceptors), which have been shown to react with critical cysteines in target proteins such as in the Nrf2/Keap system (Dinkova-Kostova, A. T., et al. (2002) *Proc. Natl. Acad. Sci. USA* 99, 11908-11913, Wakabayashi, N., et al. (2004) *Proc. Natl. Acad. Sci. USA* 101, 2040-2045, Talalay, P. & Fahey, J. W. (2001) *J. Nutr.* 131, S3027-S3033). These interactions result in irreversible alkylation via formation of a thioether bond.

As shown herein, avicins, a family of plant-derived glycosylated pentacyclic terpenoids, contain not only Michael acceptor sites but also reactive oxyesters, which participate in transesterification to yield a protein adduct linked by a reversible thioester bond.

SUMMARY OF THE INVENTION

The invention provides a thioesterification agent with the following formula

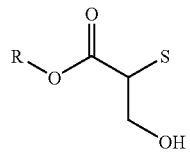

wherein R represents a chemical moiety selected from the group consisting of hydrogen, substituted aryl, unsubstituted aryl, substituted alkenyl, unsubstituted alkenyl, substituted alkyl, unsubstituted alkyl, substituted alkoxy, and unsubstituted alkoxy, and wherein S represents a chemical moiety selected from the group consisting of hydrogen, substituted aryl, unsubstituted aryl, substituted alkenyl, unsubstituted alkenyl, substituted alkyl, unsubstituted alkyl, substituted alkoxy, and unsubstituted alkoxy, and wherein the thioesterification agent is not an avicin. In one embodiment of this composition, S represents

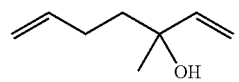

In another embodiment of this composition, the composition further comprises a targeting agent bound to the thioesterification agent at any site on the thioesterification agent. In one aspect of this embodiment, the targeting agent is selected from the group consisting of small molecules, nucleic acids and proteins. Optionally, the small molecule is selected from the group consisting of NMDA antagonists, neurological agents, anti-artherosclerotic agents, antibiotics, anti-inflammatory agents, and anti-cancer agents. Further, the nucleic acid may be a promoter region. Further, the protein may be an antibody.

In another embodiment of this composition, the thioesterification agent is selected from the group consisting of the multicyclic domain of avicin, the MT inner domain of avicin, and the MT outer domain of avicin.

The invention also provides a composition comprising a thioesterification agent bound to a targeting agent wherein the thioesterification agent reversibly modifies a signaling protein by means of a thioester bond to a cysteine residue on the signaling protein wherein the wherein the targeting agent is a small molecule selected from the group consisting of NMDA antagonists, neurological agents, anti-artherosclerotic agents, antibiotics, anti-inflammatory agents, and anti-cancer agents. In one embodiment of this composition, the signaling protein is a bacterial protein. In one aspect of this embodiment, the bacterial protein is OxyR.

In another embodiment of this composition, the thioesterification agent is selected from the group consisting of avicin, the multicyclic domain of avicin, the MT inner domain of avicin, and the MT outer domain of avicin.

In another embodiment of this composition, the NMDA receptor antagonist is selected from the group consisting of amantadine, rimantadine, memantine, ketamine, and glutamate.

In another embodiment of this composition, the neurological agents is selected from the group consisting of bupropion, citalopram, clomipramine, desipramine, doxepin, escitalopram, fluoxetine, imipramine, mirtazapine, nortriptyline, phenelzine, sertraline, trancypromine, trazodone, venlafaxine, amantadine, benztropine, bromocriptine, entacapone, levodopa/carbidopa, pramipexole, ropinirole, selegiline, trihexyphenidyl, aripiprazole, chlorpromazine, clozapine, fluphenazine, haloperidol, olanzapine, perphenazine, quetapine, risperidone, thioridazine, thiothixene, trifluoperazine and ziprasidone.

In another embodiment of this composition, the anti-artherosclerotic agent is selected from the group consisting of atorvastatin, cerivastatin, fluvastatin, lovastatin, pravastatin, simvastatin, rosuvastatin clofibrate, gemfibrozil, and fenofibrate.

In another embodiment of this composition, the antibiotic is selected from the group consisting of mitomycin C, actinomycin D, rifamycin B, streptomycin A, tetracyclines, chloramphenicol/chloromycetin, cycloheximide, erythromycin, puromycin, neomycin, penicillin, phenethicillin, ampicillin, carbenicillin, cephalosporin C, vancomycin, gramicidin A, valinomycin, nonactin, polymyxin, colistin, bacitracin, and subtilin.

In another embodiment of this composition, the anti-inflammatory agent is selected from the group consisting of diclofenac, etodolac, flurbiprofen, ibuprofen, indomethacin, ketoprofen, ketorolac, meclofenamate, nabumetone, naproxen, oxaprozin, piroxicam, rofecoxib, sulindac, tolmetin, and valdecoxib.

In another embodiment of this composition, the anti-cancer agent is selected from the group consisting of mitomycin C, mitozolamide, PCNU, taxol, vinblastine sulfate, camptothecin, doxorubicin, pyrazoloacridine, mitoxantrone, 5-fluorouracil, 5-azacytidine, methotrexate, 2'-deoxy-5-fluorouridine, ara-C, and pyrazoloimidazole.

The invention also provides a method for treating a redox state associated pathology in a subject in need thereof comprising the steps of administering to the subject a therapeutic amount of a thioesterification agent which reversibly modifies a signaling protein by means of a thioester bond to a cysteine residue on the signaling protein, wherein the thioesterification agent is not an avicin.

In one embodiment of the method for treating a redox state associated pathology, the thioesterification agent is an avicin. In one aspect of this embodiment, the avicin is a member of the group consisting of the multicyclic domain of avicin, the MT inner domain of avicin, and the MT outer domain of avicin.

In another embodiment of the method for treating a redox state associated pathology, the subject is a mammal. In one aspect of this embodiment, the mammal is a human.

In another embodiment of the method for treating a redox state associated pathology, the redox state associated pathology is selected from the group consisting of inflammation, artherosclerosis, neurological disorder, bacterial infection, and cancer.

In another embodiment of the method for treating a redox state associated pathology, wherein the thioesterification agent is a composition selected from one of the compositions described above.

The invention also provides a method of modifying the activity of a signaling protein in a cell comprising administering to the cell a composition which reversibly modifies a signaling protein in the cell by means of a thioester bond to a cysteine residue on the signaling protein, wherein the composition is not avicin.

In one embodiment of the method of modifying the activity of a signaling protein in a cell, the signaling protein is OxyR.

In another embodiment of the method of modifying the activity of a signaling protein in a cell, the cell is a bacterial cell. In one aspect of this embodiment, the bacteria is *E. coli*.

In another embodiment of the method of modifying the activity of a signaling protein in a cell, the signaling protein is Nrf2.

In another embodiment of the method of modifying the activity of a signaling protein in a cell, the cell is a mammalian cell. In one aspect of this embodiment, the mammalian cell is a human cell.

The invention also provides a method of screening for a thioesterification agent which modifies an activity of a signaling protein in a cell, wherein the activity of the signaling protein is modulation of the transcription of downstream proteins, the method comprising the steps of measuring the expression of the downstream proteins in a first group of the cells, administering to a second group of the cells the thioesterification agent, and measuring the expression of the downstream proteins in the two groups of cells, wherein if the expression of the downstream proteins is changed in the first group of cells compared to the second group of cells, the thioesterification agent modifies the thioesterification agent modifies activity of the signaling protein.

In one embodiment of the method of screening, the signaling protein is OxyR.

In another embodiment of the method of screening, the downstream proteins are encoded by the katG and oxyS genes.

In another embodiment of the method of screening, the cell is a bacterial cell. In one aspect of this embodiment, the bacterial cell is an *E. coli* cell.

In another embodiment of the method of screening, the cell is a mammalian cell. In one aspect of this embodiment, the mammalian cell is a human cell.

The invention also provides a kit comprising in one or more containers, a thioesterification agent and an agent effective in the treatment of a redox state related pathology, wherein the thioesterification agent is not an avicin.

In one embodiment of the kit, the thioesterification agent is selected from the group consisting of the multicyclic domain of avicin, the MT inner domain of avicin, and the MT outer domain of avicin.

In another embodiment of the kit, the redox state associated pathology is selected from the group consisting of inflammation, artherosclerosis, neurological disorder, bacterial infection, and cancer.

DETAILED DESCRIPTION OF THE INVENTION

Figure 1:
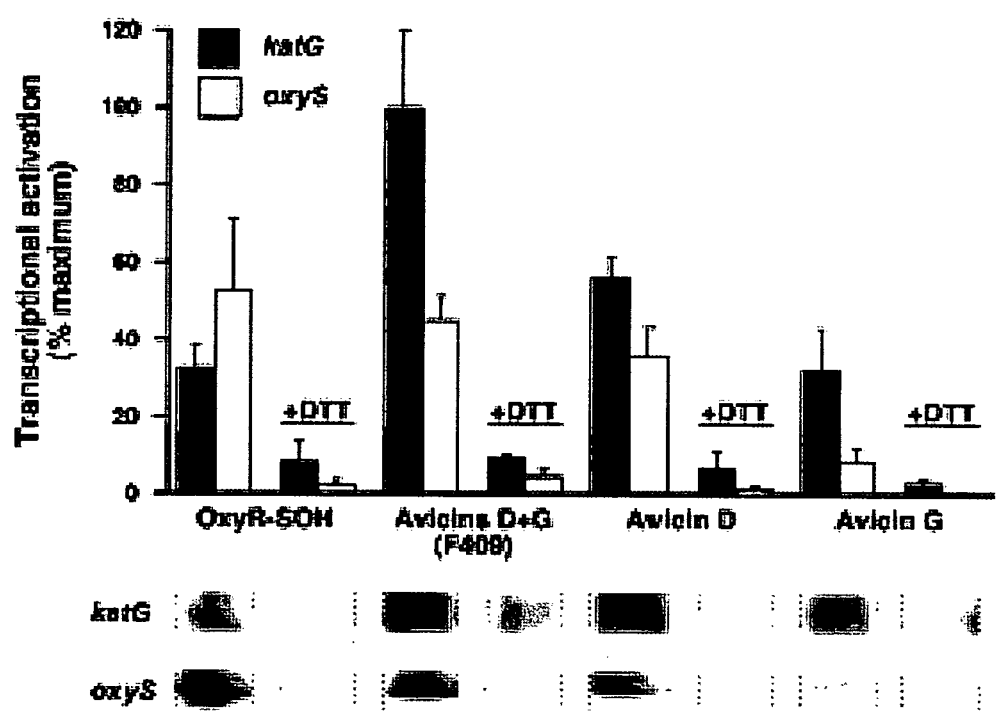
FIG. 1 is a bar graph showing the quantified transcriptional activation of expression of katG and oxyS shown in raw data below the bar graph.

The invention provides compositions which reversibly modify cysteine residues of signaling proteins through thioesterification. Compounds such as avicins, with reactive oxyesters participate in thioesterification to reversibly modify cysteine residues on signaling proteins. These modifications lead to a modulation of the function of these signaling proteins, thereby modifying their signal cascade and cellular function.

The invention is based in part upon the identification of a regulatory modification of cysteine thiol induced by avicins. Specifically, avicins reversibly transesterify the single critical regulatory Cys-199 in the bacterial transcription factor OxyR. Thus, the invention shows that reversible thioesterification of a protein Cys thiol occurs in signaling proteins, demonstrating the role for reversible thioesterification in transcriptional regulation, via formation of a thioester linkage via transesterification from an oxyester-linked donor.

Avicinylation of OxyR results in transcriptional activation of the target genes, katG and oxyS. OxyR has provided a model for understanding the ubiquitous influence of NO/redox on cellular function. Thus, the reversible thioesterification shows an additional parallel regulation pathway to NO/redox of OxyR and other signaling proteins.

Further, avicinylation triggers anti-oxidant mechanisms in bacterial cells. Avicins specifically transesterify OxyR in cells which contain enough glutathione to prevent non-specific transesterification of proteins in the cell. Anti-oxidant effects are induced by bacterial cells in response to a stressor. Thus, avicins can be used as antimicrobials by increasing stress on the bacteria either alone or in combination with other anti-microbials.

A variety of plant constituents, many of which are abundant in the diet, contain α,β-unsaturated carbonyl groups (Michael acceptors), which have been shown to react with critical cysteines in target proteins such as in the Nrf2/Keap system (Dinkova-Kostova, A. T., et al. (2002) *Proc. Natl. Acad. Sci. USA* 99, 11908-11913; Wakabayashi, N., et al. (2004) *Proc. Natl. Acad. Sci. USA* 101, 2040-2045; Talalay, P. & Fahey, J. W. (2001) *J. Nutr.* 131, S3027-S3033). These interactions result in irreversible alkylation via formation of a thioether bond. Avicins contain not only Michael acceptor sites but also reactive oxyesters, which participate in transesterification to yield a protein adduct linked by a reversible thioester bond. The reversibility of these thioesterifications allows pharmaceuticals comprising these thioesterification agents to be less toxic and thus more effective in the treatment of disease.

Bacterial OxyR shares some similarities with mammalian Nrf2: both regulate the expression of detoxifying enzymes and antioxidant proteins, both contain critical Cys residues that serve sensory and regulatory roles, and both are activated by peroxides. HPI is a functional homolog in bacteria of glutathione peroxidase (GPx), the transcription of which is regulated by Nrf2. Like hydroxyperoxidase I (HPI), GPx protects cells against hydrogen peroxide induced stress. We have previously shown that Nrf2 is activated by avicins in a DTT-reversible fashion, and it therefore seems likely that these transcriptional effects of avicin are also mediated by thioesterification. Thus, comparable thioester modifications are also performed by avicins in mammalian cells.

OxyR can be activated by several redox-related modifications of a single Cys-199 (OxyR-SX), including S-nitrosylation, S—OH, and S-glutathione. These alternatively modified forms of OxyR differ in structure, cooperative properties, and promoter activities (Kim, S. O., et al. (2002) *Cell* 109, 383-396). The findings reported here indicate that avicins participate in a reversible thioester linkage to Cys-199, which activates OxyR, thus potentially expanding the redox-based code. More generally, our results emphasize that metabolites containing electrophilic functional groups also act as thioesterification agents of proteins (Kim, S. O., et al. (2002) *Cell* 109, 383-396).

The modification of OxyR, an *E. coli* redox responsive transcriptional activator by avicin leads to its activation, and the subsequent activation of katG and oxyS. This modification is reversible through the addition of dithiothriotol (DTT). This activation leads to the activation of genes which protect the cells from oxidative insult such as hydroxyperoxidase I.

As shown above, reversible thioesterification of signaling proteins by thioesterification agents such as avicins regulates proteins associated with redox status of cells, tissues and organisms. Thus, the thioesterification agents of the invention are used to treat pathologies associated with modulation of redox state. These pathologies include artherosclerosis, neurological disorders, inflammation, bacterial infection, and cancer.

The thioesterification agents of the invention are useful for treating artherosclerosis. Shear stress prompts an anti-inflammatory, anti-atherosclerotic effect in the endothelium (Yamawaki, H., Pan, S., Lee, R. T. & Berk, B. C. *J. Clin. Invest.* 115, 733-738 (2005)). A molecule whose levels correlate with the degree of shear stress, thioredoxin interacting protein (Txnip; also known as vitamin D upregulating protein 1) interacts with other molecules to affect endothelial inflammation, a driving event in atherosclerosis.

All of this involves interactions between three players: apoptosis signaling kinase 1 (ASK1), thioredoxin and Txnip. ASK1 is a MAP kinase kinase kinase that is upstream of the stress MAP kinases that lead to stress-induced apoptosis and inflammation. Thioredoxin is ubiquitously expressed in both plants and animals, and has two cysteines in its catalytic site, which confer on thioredoxin its antioxidant properties. Importantly, when the cysteines are in the reduced (—SH) state, thioredoxin can bind to the amino-terminal portion of ASK1, inhibiting the kinase activity of ASK1 and ultimately leading to ASK1 ubiquitination and degradation, which leads to decreased inflammation involving circulatory endothelial cells thereby reducing circulatory pathologies such as atherosclerosis, associated with inflammation. The final actor in this triad is Txnip, which binds to the catalytic cysteines of thioredoxin, and thus inhibits thioredoxin activity and ability to bind to ASK1. By reversibly modifying the cysteines in thioredoxin with the thioesterification agents of the invention, thioredoxin binding of Txnip to thioredoxin would be reduced, thus decreasing inflammation in arterial walls and decreasing artherosclerosis. Thioredoxin is also regulated at the allosteric cysteine 69 by S-nitrosylation. (Haendeler J, et al. Nat Cell Biol; 4(10):743-9 (October 2002)). Thus, transesterification at this site, may be another mechanism for the treatment of artherosclerosis.

Optionally, the thioesterification agents of the invention may be bound to moieties which specifically bind to thioredoxin in order to localize the thioesterification agent to thioredoxin and thereby treat artherosclerosis.

The thioesterification agents of the invention are also useful for treating neurological disorders. For example, the NMDA receptor, is involved with neuronal development, synaptic plasticity and excitotoxic cell death. The NMDA receptor's activity is sensitive to the redox state of the brain via the redox state of cysteines 744 and 798. Reductions of these cysteines potentiates NMDA receptor mediated responses (Brimecombe, J. C. et al. JPET 291:785-792 (1999)). Thus, thioester modification of the NMDA receptor with the thioesterification agents of the invention may be used to modulate the activity of the NMDA receptor and thus treat neurological disorders.

The thioesterification agents of the invention are also useful for treating inflammation. Oxidants are formed in many metabolic and environmental processes. They are also be released by phagocytes such as neutrophils and macrophages during their role in early immune defence against pathogens, but in severe inflammation may result in host tissue damage and pathology. Thus, the thioesterification agents of the invention may be used to regulate the effect of these oxidants and modulate the inflammation caused by them.

Also, NMDA receptor antagonists such as amantadine, rimantadine, memantine ketamine, and glutamate, modified with an oxyester so that it may thioesterify the NMDA receptor may also be used to treat neurological disease. NMDA receptor antagonists would target the transesterification agent to which it was bound to the NMDA receptor, increasing the probability of specific reversible transesterification of the NMDA receptor.

The thioesterification agents of the invention are also useful for treating bacterial infections. Matrix metalloproteinases (MMPs) are critical mediators of tissue remodeling. (Okamoto, T. et al. Biological Chemistry, 385(11):997-1006 (November 2004)). Inappropriate regulation of MMPs causes many pathological events, including microbial invasion and inflammatory tissue damage. Some of the bacterial exoproteinases can effectively activate pro-MMPs (inactive zymogens) via limited proteolysis around their autoinhibitory domains. In addition, overproduction of nitric oxide (NO) may contribute to respiratory inflammation via the formation of reactive nitrogen species (RNS). Several studies have identified regulatory properties of NO/RNS on biomolecules due to functional modification of their cysteine residues. In fact, NO/RNS can mediate activation and expression of MMPs, because RNS can interact with a cysteine switch in the autoinhibitory domain, thus converting proMMPs into their active forms without proteolysis. Many studies have indicated that NO/RNS can participate in expression of various genes that affect immune-inflammatory responses, including MMPs. Although NO in some cases upregulates MMPs, S-nitrosothiols downregulate MMP-9 expression by suppressing the NF-κB pathway. While microbial proteinases cause excessive activation of MMPs and contribute to microbial pathogenesis, NO/RNS may modulate expression and activation of MMPs as well as various inflammatory mediators, depending on the redox status at sites of inflammation. Thus, modulation of redox status using the transesterification agents of the invention may be used to help treat bacterial infection and inflammation caused thereby.

MMPs are also involved in the etiology of artherosclerosis, stroke, inflammation and neurodegeneration. Thus, thioesterification of MMPs may also be used to treat artherosclerosis, stroke, inflammation or neurodegeneration. Optionally, the thioesterification agents of the invention may be bound to moieties which specifically bind MMPs in order to target the thioesterification agent to MMPs, thereby decreasing the growth of microbial cells and/or treating artherosclerosis, stroke, inflammation or neurodegeneration.

Further, as explained above, avicin activates the redox response to bacterial cells through the thioesterification of OxyR. This indicates that reversible thioesterification agents cause stress upon bacterial cells, and thus may be used as an anti-microbial alone, or in combination with other anti-microbials such as antibiotics. Optionally, the thioesterification agents of the invention may be bound to an antibiotic in order to be targeted to a microbial cell, thereby decreasing their growth.

The thioesterification agents of the invention are also useful for treating cancer. It has been shown previously that intracellular oxidation/reduction (redox) reactions regulate the $G_0$-$G_1$ to S-phase transition in the mouse embryonic fibroblast cell cycle. (Sarita G., et al. Cancer Research 63, 2109-2117, (May 1, 2003)). Intracellular redox state was modulated with a thiol-antioxidant, N-acetyl-L-cysteine (NAC), and cell cycle progression was measured using BrdUrd pulse-chase and flow cytometric analysis. Treatment with NAC for 12 h resulted in a 6-fold increase in intracellular low-molecular-weight thiols and a decrease in the signal of an oxidation-sensitive probe, dihydrofluorescein diacetate, indicating a shift in the intracellular redox state toward a more reducing environment. NAC-induced alterations in redox state caused selective delays in progression from $G_0$-$G_1$ to S phase in serum-starved cells that were serum stimulated to reenter the cell cycle as well as to inhibit progression from $G_1$ to S phase in asynchronous cultures with no significant alterations in S phase, and $G_2$+M transits. NAC treatment also showed a 70% decrease in cyclin D1 protein levels and a 3-4-fold increase in p27 protein levels, which correlated with decreased retinoblastoma protein phosphorylation. Cells released from the NAC treatment showed a transient increase in dihydrofluorescein fluorescence and oxidized glutathione content between 0 and 8 h after release, indicating a shift in intracellular redox state to a more oxidizing environment. These changes in redox state were followed by an increase in cyclin D1, a decrease in p27, retinoblastoma protein hyperphosphorylation and subsequent entry into S phase by 8-12 h after the removal of NAC. These results support the hypothesis that a redox cycle within the mammalian cell cycle might provide a mechanistic link between the metabolic processes early in $G_1$ and the activation of $G_1$-regulatory proteins in preparation for the entry of cells into S phase. Thus modulation of the redox state of cells through the use of thioesterification agents of the invention may be used in the treatment of cancer.

Further, the regulation of metalloproteinases is considered one mechanism useful for the treatment of cancers. Mannello F, et al. Curr Cancer Drug Targets. 5(4):285-98 (June 2005)). Reversible thioesterification of these proteins is another potential mechanism for the treatment of cancer using the transesterification agents of the invention. Also, retinoblastoma protein, is often mutated at cysteine 706 in certain cancer types. (Kratzke R A, et al. J Biol. Chem. 267(36): 25998-6003 (December 1992). Thus, modification of this cysteine may also be a mechanism of treatment of cancers involving retinoblastoma protein. Optionally, the thioesterification agents of the invention may also be bound to any moiety which specifically binds to metalloproteinases in order to target these proteins to metalloproteinases in order to treat of cancer.

DEFINITIONS

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of a redox state associated pathology, diminishment of extent of disease, delay or slowing of disease progression, amelioration, palliation or stabilization of the disease state, and other beneficial results described below. Redox state pathologies include artherosclerosis, neurological disorders, inflammation, bacterial infection, and cancer. Symptoms of artherosclerosis include angina, heart attack, coronary thrombosis, stroke, transient ischemic attack, leg blood clot, leg pain, leg cramps, intermittent claudication, and erectile dysfunction. Symptoms of neurological disorders include depression, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Symptoms of inflammation include redness, swollen joint that is warm to touch, joint pain, joint stiffness, loss of joint function, fever, chills, fatigue/loss of energy, headaches, loss of appetite and muscle stiffness. Symptoms of bacterial infection include headache, pain, upper jaw and tooth ache, tenderness around the nose, forehead and cheeks, swelling and pressure around the eyes, ear ache and infection, fever, weakness or fatigue, a cough, runny nose or nasal congestion, fever, chills, coughs, difficulty breathing, chest and abdominal pain, and loss of appetite. Symptoms of cancer include persistent cough, blood-tinged saliva, a change in bowel habits, blood in stool, unexplained anemia, breast lump, breast discharge, lumps in the testicles, a change in urination, blood in the urine, hoarseness, persistent lumps or swollen glands, obvious change in a wart or a mole, indigestion or difficulty swallowing, unusual vaginal bleeding or discharge, unexpected weight loss, night sweats, fever, continued itching in your anus or genitals, nonhealing sores, headaches, back pain, pelvic pain, bloating, and indigestion.

As used herein, "reduction" of a symptom or symptoms (and grammatical equivalents of this phrase) means decreasing of the severity or frequency of the symptom(s), or elimination of the symptom(s).

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "manifestation" of a disease refers to a symptom, sign, anatomical state (e.g., tumor), physiological state (e.g., sepsis), or report (e.g., LDL level) characteristic of a subject with the disease.

As used herein, a "therapeutically effective amount" of a drug or agent is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

As used herein, a "prophylactically effective amount" of a drug is an amount of a drug that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose and may occur only after administration of a series of doses. Thus, a prophylactically effective amount may be administered in one or more administrations.

Administration of an agent "in combination with" includes parallel administration (administration of both the agents to the patient over a period-of time, such as administration of a monoclonal antibody and a peptide hormone such as an incretin hormone or analog on alternate days for one month), co-administration (in which the agents are administered at approximately the same time, e.g., within about a few minutes to a few hours of one another), and co-formulation (in which the agents are combined or compounded into a single dosage form suitable for oral or parenteral administration).

A "reversible thioester bond" is one in which the bond is broken after the administration of, at most, 200 mM dithiothriotol (DTT).

Thioesterification Agents

The thioesterification agents of the invention are able to reversibly modify cysteine residues of proteins through a reversible thioester bond. This bond is reversible in the presence of at most about 200 mM dithiothriotol (DTT). Preferably the bond is reversible in the presence of at most between about 10 and about 100 mM DTT. The best characterized thioesterification agents are avicins defined below. Other thioesterification agents are also disclosed below.

Avicins

Figure 3:
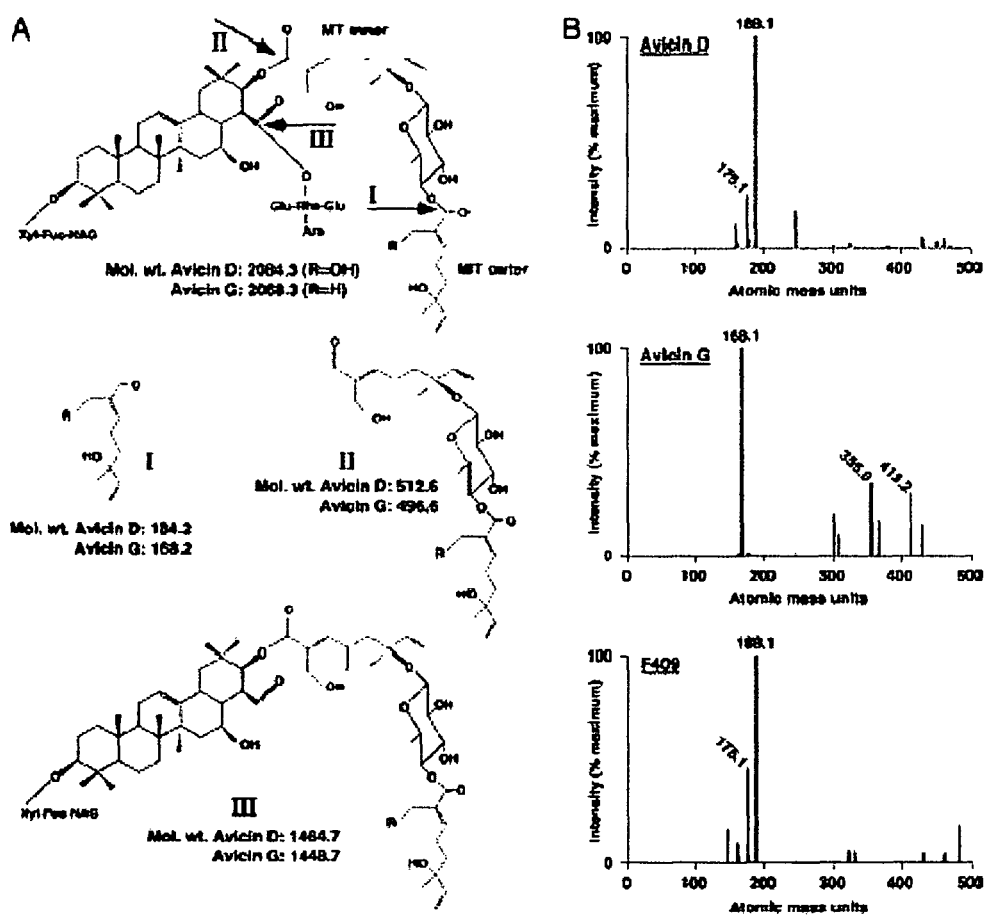
FIG. 3A is a schematic showing the structures of avicins D and G and fragments I, II, and III which are potentially complexed with cysteine thiols.
FIG. 3B shows electrospray ionization/mass spectrometry data for OxyR in the presence of avicin D, G and F094 (a mixture of avicin D and G).

The structure of avicins D and G are shown in FIG. 3. Avicins are isolated from the pods and roots of *Acacia victoriae*. Methods of isolating avicins are shown in U.S. Pat. No. 6,746,696, incorporated herein in its entirety.

Avicins comprise a purified triterpene compound comprising a triterpene moiety attached to a monoterpene moiety having the molecular formula:

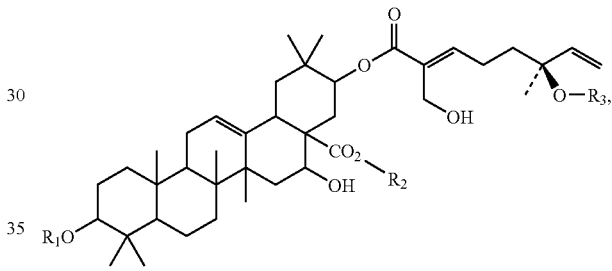

or a pharmaceutical formulation thereof, wherein a) $R_1$ and $R_2$ are selected from the group consisting of hydrogen, C1-C5 alkyl, and an oligosaccharide; b) $R_3$ is selected from the group consisting of hydrogen, hydroxyl, C1-C5 alkyl, C1-C5 alkylene, C1-C5 alkyl carbonyl, a sugar, and a monoterpene group; and c) the formula further comprises $R_4$, wherein $R_4$ is selected from the group consisting of hydrogen, hydroxyl, C1-C5 alkyl, C1-C5 alkylene, C1-C5 alkyl carbonyl, a sugar, C1-C5 alkyl ester, and a monoterpene group, and wherein $R_4$ may be attached to the triterpene moiety or the monoterpene moiety. Avicins also encompass the above formula wherein $R_3$ is a sugar. In other avicin structures, the sugar is selected from the group consisting of glucose, fucose, rhamnose, arabinose, xylose, quinovose, maltose, glucuronic acid, ribose, N-acetyl glucosamine, and galactose. In other avicin structures, the compound further comprises a monoterpene moiety attached to the sugar.

Another avicin structure comprises a composition wherein $R_3$ has the following formula

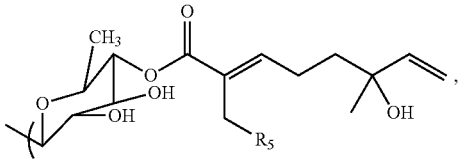

wherein $R_5$ is selected from the group consisting of hydrogen, hydroxyl, C1-C5 alkyl, C1-C5 alkylene, C1-C5 alkyl carbonyl, a sugar, C1-C5 alkyl ester, and a monoterpene group.

Avicins also encompass the above formula wherein $R_5$ is a hydrogen or a hydroxyl. Avicins also encompass the above formula wherein $R_1$ and $R_2$ each comprise an oligosaccharide. In other avicin structures, $R_1$ and $R_2$ each comprise a monosaccharide, a disaccharide, a trisaccharide or a tetrasaccharide. In other avicin structures, $R_1$ and $R_2$ each comprise an oligosaccharide comprising sugars which are separately and independently selected from the group consisting of glucose, fucose, rhamnose, arabinose, xylose, quinovose, maltose, glucuronic acid, ribose, N-acetyl glucosamine, and galactose. In other avicin structures, at least one sugar is methylated.

In some avicin structures, $R_4$ is attached to the triterpene moiety through one of the methylene carbons attached to the triterpene moiety. In another avicin structure, the triterpene moiety is oleanolic acid instead of acacic acid.

Another avicin structure includes a composition comprising a triterpene glycoside having the molecular formula:

Another family of avicin structures includes a composition comprising a triterpene glycoside having the molecular formula:

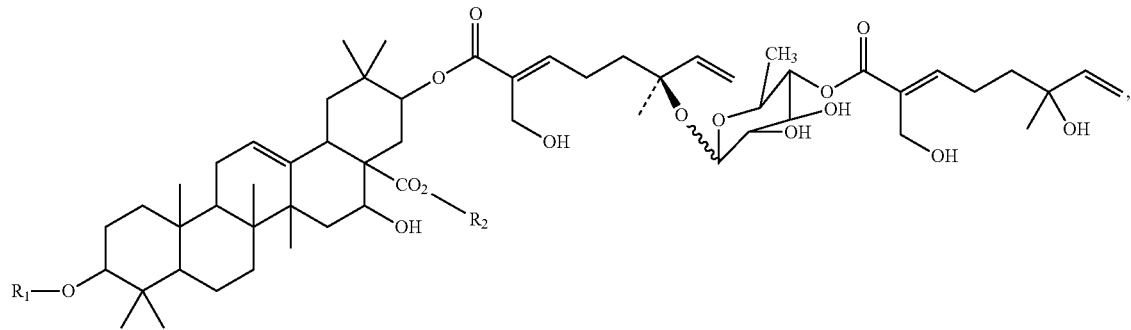

or a pharmaceutical formulation thereof, wherein a) $R_1$ is an oligosaccharide comprising N-acetyl glucosamine, fucose and xylose; and b) $R_2$ is an oligosaccharide comprising glucose, arabinose and rhamnose.

In another avicin structure, the compound has the molecular formula:

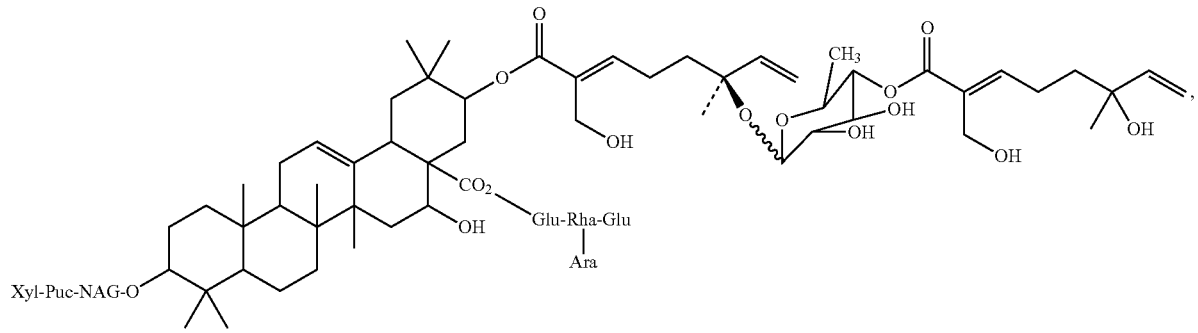

or a pharmaceutical formulation thereof is described.

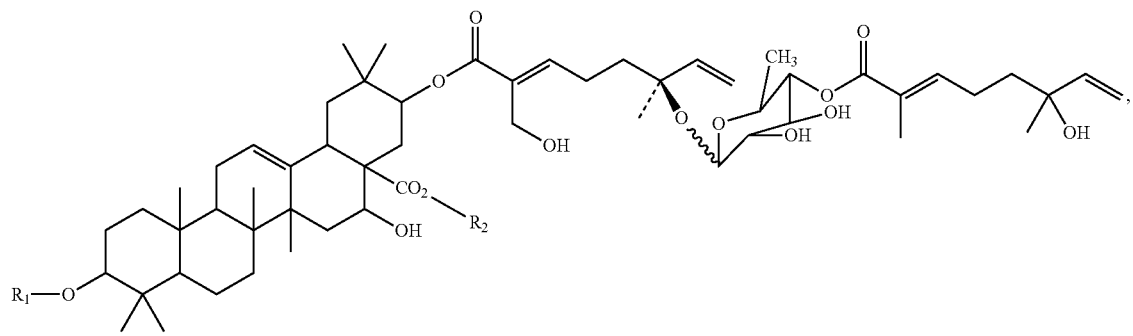

or a pharmaceutical formulation thereof wherein, a) $R_1$ is an oligosaccharide comprising N-acetyl glucosamine, fucose and xylose; and b) $R_2$ is an oligosaccharide comprising glucose, arabinose and rhamnose. One embodiment of this family of avicin structures includes a composition having the molecular formula:

cose, glucose and xylose; and b) $R_2$ is an oligosaccharide comprising glucose, arabinose and rhamnose.

Avicins also encompass the structure comprising having the molecular formula:

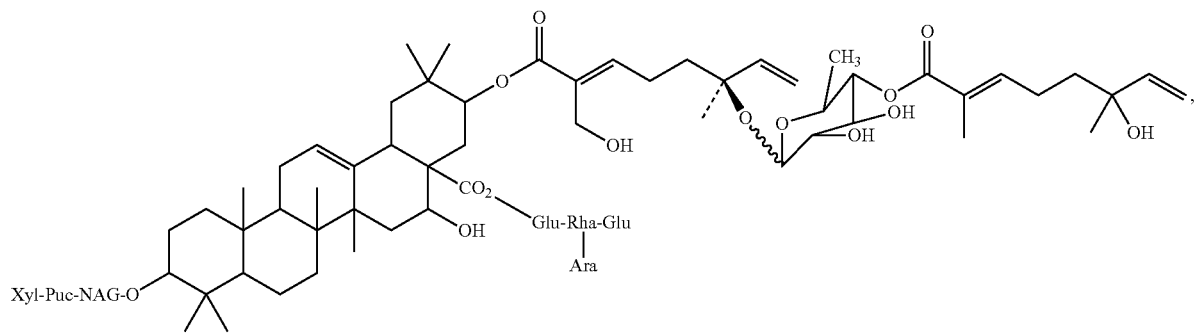

or a pharmaceutical formulation thereof.

Another family of avicin structures includes a composition comprising a triterpene glycoside having the molecular formula:

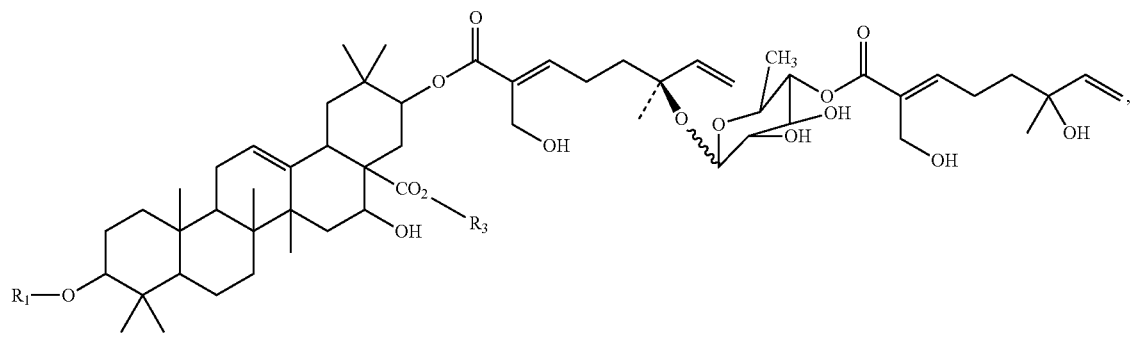

or a pharmaceutical formulation thereof, wherein, a) $R_1$ is an oligosaccharide comprising N-acetyl glucosamine, glu-

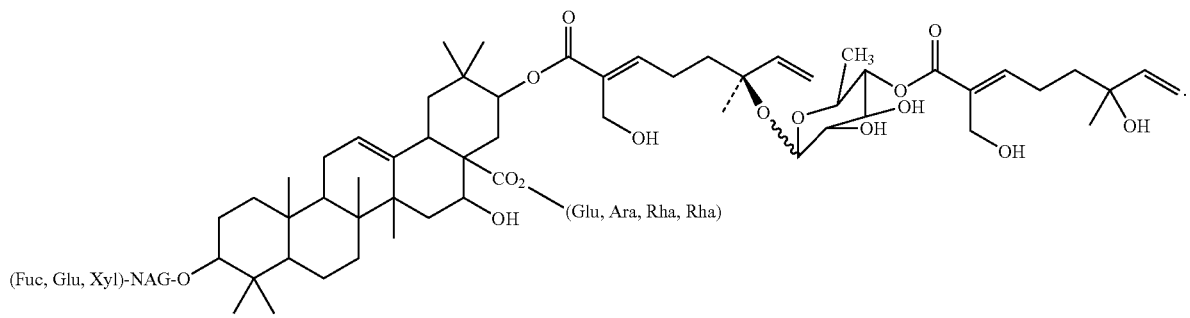

Other Thioesterification Agents

Figure 4:
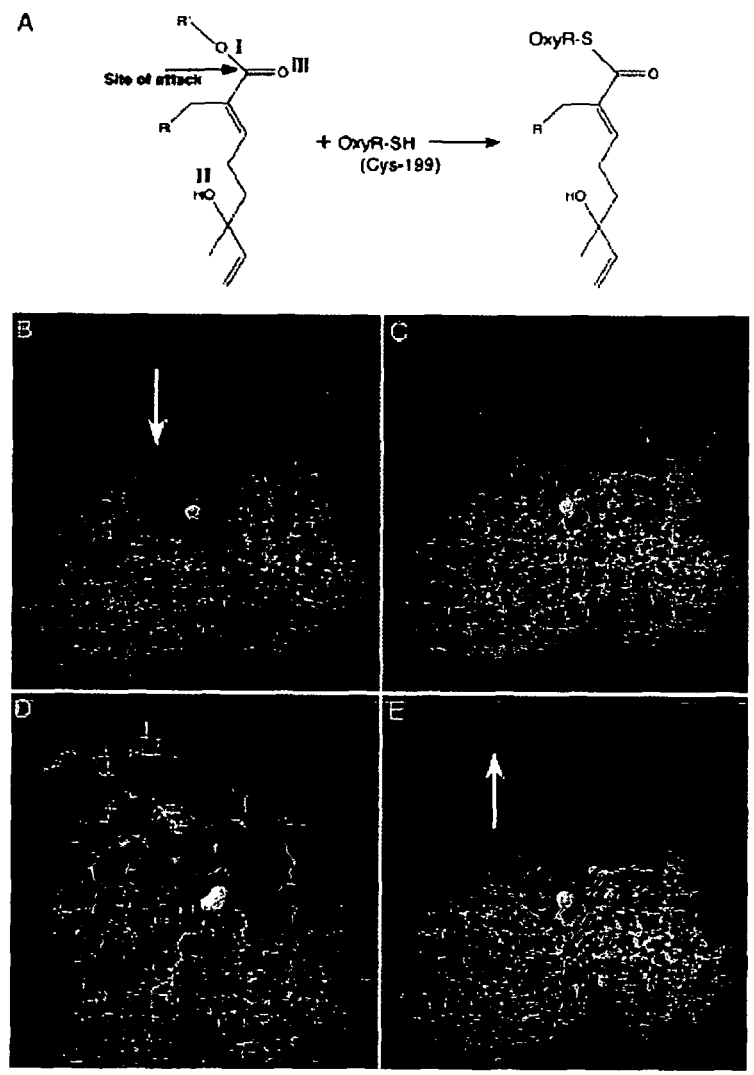
FIG. 4A is a schematic showing a reaction scheme for the thioesterification of cysteine-199 of OxyR.
FIG. 4B is a molecular model of the docking of avicin D to OxyR.
FIG. 4C is a molecular model of the docking of avicin D into the hydrophobic pocket of OxyR.
FIG. 4D is a molecular model showing the proximity of Cys 199 to the various subunits of avicin D.
FIG. 4E is a molecular model of the cleavage of avicin D, leaving the outer monoterpenoid unit coupled to Cys 199 of OxyR.

Any compound containing an oxyester with the formula $R_1COOR_2$, wherein $R_1$ and $R_2$ are hydrogen or any alkyl or acyl group, is a potential transesterification agent. In one specific embodiment, $R_1$ is hydrogen and $R_2$ is memantine making a memantine oxyester. Other specific transesterification agents are shown in FIG. 4. In FIG. 4, 3 possible transesterification sites are marked as I, II, and III. Thus, the avicin molecule may be split in order use any of the three transesterification sites. The "MT inner" and "MT outer" domains may be used alone as transesterification agents. Further, the multicyclic moiety, without the MT inner or outer groups may also be used as a thioesterification agent.

carbon atoms. The term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having

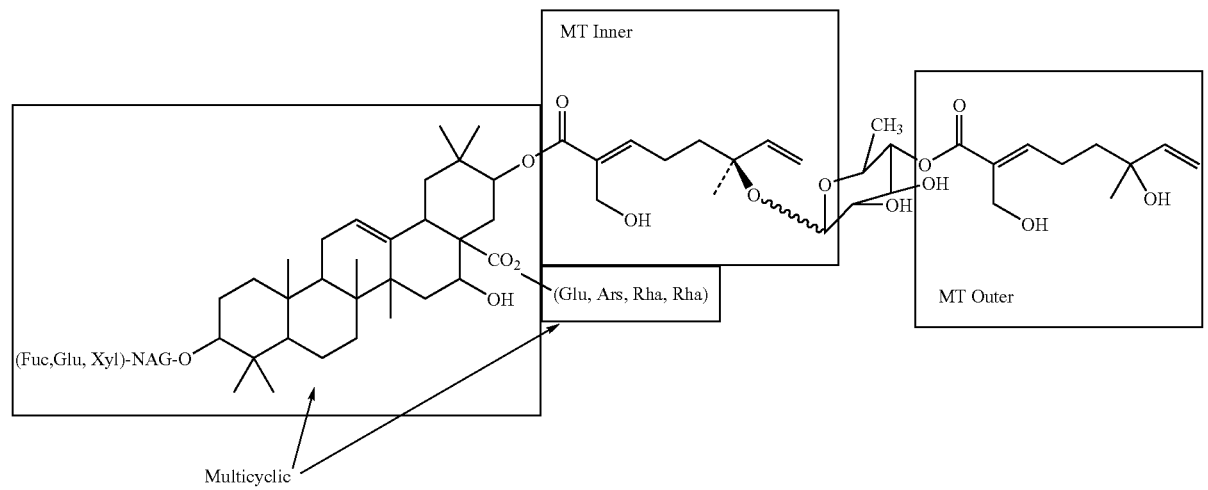

In another embodiment of the invention, the thioesterification agent has the following formula.

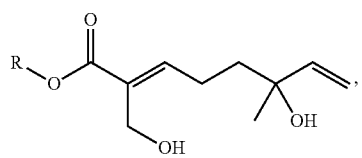

The R group in the above formula may be hydrogen, substituted and unsubstituted aryl, substituted and unsubstituted alkenyl, substituted and unsubstituted alkyl and substituted or unsubstituted alkoxy. The alkyl groups preferably have from 1 to about 15 carbon atoms, more preferably from 1 to about 10 carbon atoms, still more preferably from 1 to about 6 one or more oxygen linkage and preferably have from 1 to 15 carbon atoms, more preferably from 1 to about 6 carbon atoms. The R group may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms. In one aspect of this embodiment, the above formula does not encompass any member of the avicin family of molecules.

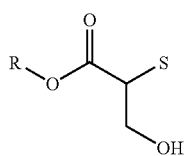

The R group in the above formula may be hydrogen, substituted and unsubstituted aryl, substituted and unsubstituted alkenyl, substituted and unsubstituted alkyl and substituted or unsubstituted alkoxy. The alkyl groups preferably have from 1 to about 15 carbon atoms, more preferably from 1 to about 10 carbon atoms, still more preferably from 1 to about 6 carbon atoms. The term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The R group may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms.

The S group in the above formula may be hydrogen, substituted and unsubstituted aryl, substituted and unsubstituted alkenyl, substituted and unsubstituted alkyl and substituted or unsubstituted alkoxy. The alkyl groups preferably have from 1 to about 15 carbon atoms, more preferably from 1 to about 10 carbon atoms, still more preferably from 1 to about 6 carbon atoms. The term alkyl unless otherwise modified refers to both cyclic and noncyclic groups, although of course cyclic groups will comprise at least three carbon ring members. Straight or branched chain noncyclic alkyl groups are generally more preferred than cyclic groups. Straight chain alkyl groups are generally more preferred than branched. The alkenyl groups preferably have from 2 to about 15 carbon atoms, more preferably from 2 to about 10 carbon atoms, still more preferably from 2 to 6 carbon atoms. Especially preferred alkenyl groups have 3 carbon atoms (i.e., 1-propenyl or 2-propenyl), with the allyl moiety being particularly preferred. Phenyl and napthyl are generally preferred aryl groups. Alkoxy groups include those alkoxy groups having one or more oxygen linkage and preferably have from 1 to 15 carbon atoms, more preferably from 1 to about 6 carbon atoms. The S group may be substituted at one or more available positions by one or more suitable groups such as, for example, alkyl groups such as alkyl groups having from 1 to 10 carbon atoms or from 1 to 6 carbon atoms, alkenyl groups such as alkenyl groups having from 2 to 10 carbon atoms or 2 to 6 carbon atoms, aryl groups having from six to ten carbon atoms, halogen such as fluoro, chloro and bromo, and N, O and S, including heteroalkyl, e.g., heteroalkyl having one or more hetero atom linkages (and thus including alkoxy, aminoalkyl and thioalkyl) and from 1 to 10 carbon atoms or from 1 to 6 carbon atoms. In one embodiment, the above formula does not encompass any member of the avicin family of molecules. In one embodiment, the above formula does not encompass any member of the avicin family of molecules.

Methods of the Invention and Agents Useful Therein

Overview of the Methods of the Invention

The thioesterification agents are used according to the invention to create thioester modifications on cysteine residues of signaling proteins. Preferably, these signaling proteins include OxyR and Nrf2. Other signaling proteins which are modifiable using the methods of the invention include NF-κB, inducible nitric oxide synthase (iNOS), thioredoxin and NMDA receptor. Any signaling protein is contemplated as modifiable by the thioesterification agents of the invention.

The thioesterification agents of the invention are generally administered to a subject at a dosage from about 1 μg/kg/day to about 100 mg/kg/day. Preferably, the thioesterification agents of the invention are administered at a dosage from about 10 μg/kg/day to about 10 mg/kg/day. More preferably, the thioesterification agents of the invention are administered at a dosage from about 100 μg/kg/day to about 1 mg/kg/day. The subject is preferably a mammal. This mammal is preferably a human.

The thioesterification agents of the invention may be coupled with targeting agents in order to localize the thioesterification agent to the target signal protein. Targeting agents include proteins, nucleic acids, and small molecules which are capable or specifically localizing the thioesterification agent to a target signaling protein.

In one embodiment, targeting agents are moieties, which specifically bind to a signaling protein. For example, moieties which specifically bind to OxyR (or other proteins in microbial cells), Nrf2, thioredoxin, MMPs, metalloproteinases, or NMDA receptor in such a way that a coupled thioesterification agent may interact with critical cysteine residues on these signaling proteins may be used. In another embodiment, targeting agents specifically bind to any protein involved with a pathology. These proteins include bacterial, fungal or viral proteins, cell receptor proteins, proteins involved with cell metabolism or proteins involved with cell cycle.

In one embodiment, NMDA receptor antagonists may be used as targeting agents bound to a thioesterification agent for use in treating neurological disorders, targeting the thioesterification agent to the NMDA receptor. NMDA receptor antagonists include amantadine, rimantadine, memantine, ketamine, and glutamate.

In another embodiment, neurological agents may be used as targeting agents bound to a thioesterification agent for use in treating neurological disorders, targeting the thioesterification agent to neurons and proteins involved in their activity. Neurological agents include bupropion, citalopram, clomipramine, desipramine, doxepin, escitalopram, fluoxetine, imipramine, mirtazapine, nortriptyline, phenelzine, sertraline, trancypromine, trazodone, venlafaxine, amantadine, benztropine, bromocriptine, entacapone, levodopa/carbidopa, pramipexole, ropinirole, selegiline, trihexyphenidyl, aripiprazole, chlorpromazine, clozapine, fluphenazine, haloperidol, olanzapine, perphenazine, quetapine, risperidone, thioridazine, thiothixene, trifluoperazine and ziprasidone.

In another embodiment, anti-artherosclerotic agents may be used as targeting agents bound to a thioesterification agent for use in treating artherosclerosis, by targeting the thioesterification agent to proteins in tissues and cells involved in artherosclerosis. Anti-artheroscrotic agents include atorvastatin, cerivastatin, fluvastatin, lovastatin, pravastatin, simvastatin, rosuvastatin clofibrate, gemfibrozil, and fenofibrate.

In another embodiment, antibiotics may be used as targeting agents bound to a thioesterification agent for use in treating microbial cell infection, by targeting the thioesterification agent to microbial cells. These antibiotics include mitomycin C, actinomycin D, rifamycin B, streptomycin A, tetracyclines, chloramphenicol/chloromycetin, cycloheximide, erythromycin, puromycin, neomycin, penicillin, phenethicillin, ampicillin, carbenicillin, cephalosporin C, vancomycin, gramicidin A, valinomycin, nonactin, polymyxin, colistin, bacitracin, and subtilin.

In another embodiment, anti-inflammatory agents may be used as targeting agents bound to a thioesterification agent for use in treating inflammation and related disorders, by targeting the thioesterification agent to proteins in cells and tissues involved with inflammation and the immune system. Anti-inflammatory agents include diclofenac, etodolac, flurbiprofen, ibuprofen, indomethacin, ketoprofen, ketorolac, meclofenamate, nabumetone, naproxen, oxaprozin, piroxicam, rofecoxib, sulindac, tolmetin, and valdecoxib.

In another embodiment, anti-cancer agents may be used as targeting agents bound to a thioesterification agent for use in treating cancer and related proliferative disorders by targeting the thioesterification agent to proteins in cells and tissues involved with cancer. Anti-cancer agents which may be used in the combination therapy of the invention include mitomycin C, mitozolamide, PCNU, taxol, vinblastine sulfate, camptothecin, doxorubicin, pyrazoloacridine, mitoxantrone, 5-fluorouracil, 5-azacytidine, methotrexate, 2'-deoxy-5-fluorouridine, ara-C, and pyrazoloimidazole.

In another embodiment, targeting agents are agonists of the signaling proteins. For example, a receptor which is targeted for thioesterification may be targeted by coupling the transesterification agent to its agonist. In the case of NMDA receptor, NMDA would be coupled with the thioesterification agent. Either small molecule or protein agonists may be used as targeting agents for thioesterification agents.

In another embodiment, a nucleic acid is used as a targeting agent in order to target the thioesterification agent to a DNA binding protein.

Diseases and Conditions Amenable to Treatment

The thioesterification agents either alone or in combination with targeting agents of the present invention can be used to treat any mammal, including humans and animals, suffering from a disease, symptom, or condition related to a modulation of the activity of a signaling protein through the reversible thioester modification of a cysteine residue in the signaling protein. Such diseases and conditions include cancer, inflammation, bacterial infection, artherosclerosis, and neurological disorders.

Combination Therapies

The thioesterification agents of the invention may be combined with other therapeutic agents to treat any of the diseases or conditions described above. The other therapeutic agent is chosen on the basis of its ability to treat a targeted pathology in a subject. This combination may include thioesterification agents which are complexed with a targeting agent described above. Other therapeutic agents are administered at or below the dosage normally administered by one of ordinary skill in the art.

For example, a combination therapy for cancer would include a thioesterification agent and an anti-cancer agent. The thioesterification agents are selected from any of the thioesterification agents described above. Anti-cancer agents which may be used in the combination therapy of the invention include mitomycin C, mitozolamide, PCNU, taxol, vinblastine sulfate, camptothecin, doxorubicin, pyrazoloacridine, mitoxantrone, 5-fluorouracil, 5-azacytidine, methotrexate, 2'-deoxy-5-fluorouridine, ara-C, and pyrazoloimidazole.

A combination therapy for inflammation would include a thioesterification agent and an anti-inflammatory agent. Anti-inflammatory agents which may be used in the combination therapy of the invention include diclofenac, etodolac, flurbiprofen, ibuprofen, indomethacin, ketoprofen, ketorolac, meclofenamate, nabumetone, naproxen, oxaprozin, piroxicam, rofecoxib, sulindac, tolmetin, and valdecoxib.

A combination therapy for bacterial infection would include a thioesterification agent and an antibiotic agent. Antibiotic agents which may be used in the combination therapy of the invention include mitomycin C, actinomycin D, rifamycin B, streptomycin A, tetracyclines, chloramphenicol/chloromycetin, cycloheximide, erythromycin, puromycin, neomycin, penicillin, phenethicillin, ampicillin, carbenicillin, cephalosporin C, vancomycin, gramicidin A, valinomycin, nonactin, polymyxin, colistin, bacitracin, and subtilin.

A combination therapy for artherosclerosis would include a thioesterification agent and an anti-artheroscrotic agent. Anti-artheroscrotic agents which may be used in the combination therapy of the invention include atorvastatin, cerivastatin, fluvastatin, lovastatin, pravastatin, simvastatin, rosuvastatin clofibrate, gemfibrozil, and fenofibrate.

A combination therapy for a neurological disorder would include a thioesterification agent and a neurological agent. Neurological agents which may be used in the combination therapy of the invention include bupropion, citalopram, clomipramine, desipramine, doxepin, escitalopram, fluoxetine, imipramine, mirtazapine, nortriptyline, phenelzine, sertraline, trancypromine, trazodone, venlafaxine, amantadine, benztropine, bromocriptine, entacapone, levodopa/carbidopa, pramipexole, ropinirole, selegiline, trihexyphenidyl, aripiprazole, chlorpromazine, clozapine, fluphenazine, haloperidol, olanzapine, perphenazine, quetapine, risperidone, thioridazine, thiothixene, trifluoperazine and ziprasidone.

Pharmaceutical Compositions, Dosing and Administration

The thioesterification agents of the present invention are administered separately or co-formulated in a suitable co-formulated dosage form. Compounds, including those used in combination therapies are administered to a patient in the form of a pharmaceutically acceptable salt or in a pharmaceutical composition. A compound that is administered in a pharmaceutical composition is mixed with a suitable carrier or excipient such that a therapeutically effective amount is present in the composition. The term "therapeutically effective amount" refers to an amount of the compound that is necessary to achieve a desired endpoint (e.g., decreasing symptoms associated with cancer).

A variety of preparations can be used to formulate pharmaceutical compositions containing mutein or wild-type proteases and other therapeutic agents. Techniques for formulation and administration may be found in "Remington: The Science and Practice of Pharmacy, Twentieth Edition," Lippincott Williams & Wilkins, Philadelphia, Pa. Tablets, capsules, pills, powders, granules, dragees, gels, slurries, ointments, solutions, suppositories, injections, inhalants and aerosols are examples of such formulations. The formulations can be administered in either a local or systemic manner or in a depot or sustained release fashion. Administration of the composition can be performed in a variety of ways. The compositions and combination therapies of the invention may be administered in combination with a variety of pharmaceutical excipients, including stabilizing agents, carriers and/or encapsulation formulations as described herein.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including creams, lotions, mouthwashes, inhalants and the like.

For human administration, preparations should meet sterility, pyrogenicity, general safety and purity standards as required by the FDA.

Administration of thioesterification agents alone or in combination therapies may be, e.g., subcutaneous, intramuscular or intravenous injection, or any other suitable route of administration. A particularly convenient frequency for the administration of the compounds of the invention is once a day.

Upon formulation, therapeutics will be administered in a manner compatible with the dosage formulation, and in such amount as is pharmacologically effective. The formulations are easily administered in a variety of dosage forms, such as the injectable solutions described, but drug release capsules and the like can also be employed. In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals.

A carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Suitable preservatives for use in solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like.

The thioesterification agents and combination therapies of the invention can be formulated by dissolving, suspending or emulsifying in an aqueous or nonaqueous solvent. Vegetable (e.g., sesame oil, peanut oil) or similar oils, synthetic aliphatic acid glycerides, esters of higher aliphatic acids and propylene glycol are examples of nonaqueous solvents. Aqueous solutions such as Hank's solution, Ringer's solution or physiological saline buffer can also be used. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for subcutaneous or intramuscular injection is also contemplated. In this regard, the use of DMSO as solvent is preferred as this will result in extremely rapid penetration, delivering high concentrations of the active compound(s) or agent(s) to a small area.

Where one or both active ingredients of the combination therapy is given orally, it can be formulated through combination with pharmaceutically acceptable carriers that are well known in the art. The carriers enable the compound to be formulated, for example, as a tablet, pill, capsule, solution, suspension, sustained release formulation; powder, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxypropylmethylcellulose, sodium carboxymethylcellulose and polyvinylpyrrolidone (PVP). Oral formulations include such normally employed excipients as, for example, pharmaceutical grades of mannitol, lactose, starch, magnesium stearate, sodium saccharine, cellulose, magnesium carbonate and the like.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

The subject treated by the methods of the invention is a mammal, more preferably a human. The following properties or applications of these methods will essentially be described for humans although they may also be applied to non-human mammals, e.g., apes, monkeys, dogs, mice, etc. The invention therefore can also be used in a veterinarian context.

Kits

The invention further relates to kits for treating patients with redox state associated disorders such as artherosclerosis, neurological disorders, inflammation, bacterial infections, and cancer, comprising a therapeutically effective dose of a thioesterification agent, for example, avicin D, G or H, or any mixture of the three. Optionally, the thioesterification agent may be bound to a targeting agent, as described above. Additionally, the kit may also contain additional agents for treatment of redox state associated disorders such as artherosclerosis, neurological disorders, inflammation, bacterial infections, and cancer, including those listed above.

The following examples are nonlimiting and meant only to illustrate various aspects of the invention.

EXAMPLES

Materials and Methods

Avicins. Ground seed pods of *Acacia victoriae* were extracted in 20% MeOH as described (Jayatilake, G. S., et al. (2003) *J. Nat. Prod.* 66, 779-783.). Solvent/solvent partitioning of the extract concentrated the bioactivity in a polar fraction designated (F094). Avicins D and G were purified from F094 as described (Jayatilake, G. S., et al.).

Reduction of OxyR. The reduced form of OxyR was generated by addition of a large excess of DTT (200 mM) for 1 h, followed by exhaustive dialysis (25 mM potassium phosphate/250 mM potassiumsulfate/1 mM magnesium sulfate/ 100 µM DTPA, pH 8) in an anaerobic glove box. Removal of DTT was monitored by the color change after addition of 5,5'-dithionitrobenzoic acid to an aliquot of the dialysis buffer.

Treatment of OxyR with Avicins. Reduced OxyR was treated with a 10-fold molar excess of F094 or purified avicin D or G to generate avicin-modified OxyR. The reaction was performed under anaerobic conditions for 1 h, followed by dialysis.

In Vitro Transcription and Primer Extension. In vitro transcription with the various modified forms of OxyR was performed as described (Kim, S. O., et al. (2002) *Cell* 109, 383-396). Plasmid pBT22 was used as the katG template and pUCOXYS, a plasmid containing the oxyS-coding region cloned into pUC19, was used as the oxyS template. Where indicated, avicin-modified forms of OxyR were reduced with 200 mM DTT. Primer extension assays were performed by using AMV reverse transcriptase (Promega), according to instructions supplied by the manufacturer.

Hydroperoxidase I (HPI) Assay. The peroxidase activity of HPI was measured as described (Hausladen, A. et al. (1996) *Cell* 86, 719-729), in 50 mM potassium phosphate buffer (pH 7.5) containing 0.1 mM EDTA, 10 mM $H_2O_2$, and 0.2 mg/ml o-dianisidine, by measuring the increase in absorbance at 460 nm (Clairborne, A. & Fridovich, I. (1979) *Biochemistry* 18, 2324-2329). An extinction coefficient of 11.3 $mM^{-1}$ $cm^{-1}$ was used to calculate the specific activity of HPI ((1993) in *Worthington Enzyme Manual: Peroxidase*, ed. Worthington, V. (Worthington Biochemical Corporation, Freehold, N.J.)).

Electrospray Ionization (ESI)/MS. ESI/MS was performed with a mass spectrometer equipped with an orthogonal electrospray source (Z-spray) operated in positive ion mode (LCT, Waters Micromass MS Technologies). Sodium iodide was used for mass calibration for a calibration range of m/z 100-2,500. Trypsin (2 µl, 1 mg/ml) was added to avicin-modified OxyR (500 µl, 150 µg/ml), and the mixture was incubated for 5 h at 37° C. Trypsin-digested proteins were suspended in 50% acetonitrile/50% and 0.1% formic acid at a concentration of ≈50 pmol/µl and infused into the electrospray source at a rate of 5-10 $µl/min^{-1}$. Optimal ESI/MS conditions were: capillary voltage 3,000 V, source temperature 110° C., and a cone voltage of 55 V. The ESI gas was nitrogen. A quadrupole was set to optimally pass ions from m/z 500-2,000, and all ions transmitted into the pusher region of the TOF analyzer were scanned over m/z 500-3,000, with a 1-s integration time. Data were acquired in continuous mode until acceptable averaged data were obtained (10-15 min). ESI/MS data were deconvoluted by using MaxEnt I (Waters Micromass MS Technologies).

MALDI-TOF/MS. Avicin-modified OxyR was trypsin digested as above, followed by addition of 5 µl of 10% trifluoroacetic acid (TFA) to stop the digest. MALDI-TOF was performed with a mass spectrometer operated in linear positive ion mode with an $N_2$ laser (Reflex III, Bruker, Bremen, Germany). Laser power was restricted to the minimum level required to generate a signal, and the accelerating voltage was set at 28 kV. The instrument was calibrated with protein/peptide standards bracketing the molecular weights of the protein/peptide samples (typically, mixtures of apomyoglobin and BSA using doubly charged, singly charged, and dimer peaks as appropriate, or bradykinin fragment 1-5 and adrenocorticotropic hormone fragment 18-39 for tryptic digest analysis). Samples were prepared in 0.1% TFA at an approximate concentration of 50 pmol/μl. Sinapinic acid was used as the matrix for proteins and α-cyano-4-hydroxy-cinnamic acid as the matrix for peptides prepared as saturated solutions in 50% acetonitrile/0.1% TFA (in water). Aliquots of 1 μl of matrix and 1 μl of sample were mixed thoroughly, and 0.5 μl of the mixture was spotted on the target plate and allowed to dry.

Example 1

Avicins Transcriptionally Activate OxyR in a DTT Reversible Manner

Exposure of reduced OxyR to room air [which generates Cys-199-SOH (Kim, S. O., et al. (2002) Cell 109, 383-396)] or to F094 (an unspecified mixture of avicin D and G), avicin D or G (avicins: OxyR, 1:10-100:1) under strictly anaerobic conditions resulted in OxyR activation as assessed by in vitro transcriptional activation of katG and oxyS (FIG. 1). Avicin modified OxyR was incubated with plasmids containing the katG or oxyS genes followed by primer extension (see Materials and Methods). After primer extension, samples were untreated or treated with DTT before gel analysis. Band intensities were quantified (phosphoimager), and data are plotted at top as percent maximal activation (n=2-3). At bottom, corresponding raw data from an individual experiment are depicted.

F094 and avicin D were more potent activators than avicin G. Additional results suggest that avicins can exert a graded and cooperative effect on both promoters. Addition of DTT after avicin modification reversed OxyR activation (FIG. 1). Thus, a thiol-based modification by avicin activates OxyR, and DTT sensitivity indicates that the modification is reversible rather than thioether-based.

Activation of OxyR by avicin in situ was demonstrated by examining the induction of HPI. HPI, the enzyme encoded by the katG gene, protects bacterial cells against hydrogen peroxide-induced stress. E. coli strains RK4936 (wild-type) and TA4112 (OxyR-null) were grown aerobically to an A600 of 0.5 and then treated with 100 μM F094 or avicin D or G for 60 min. Cells were harvested by centrifugation, and the peroxidase activity in crude extracts was determined (see Materials and Methods). Wild-type (RK4936) and OxyR-null (TA4112) strains of bacteria were treated with avicins and assayed for HPI activity.

Figure 2:
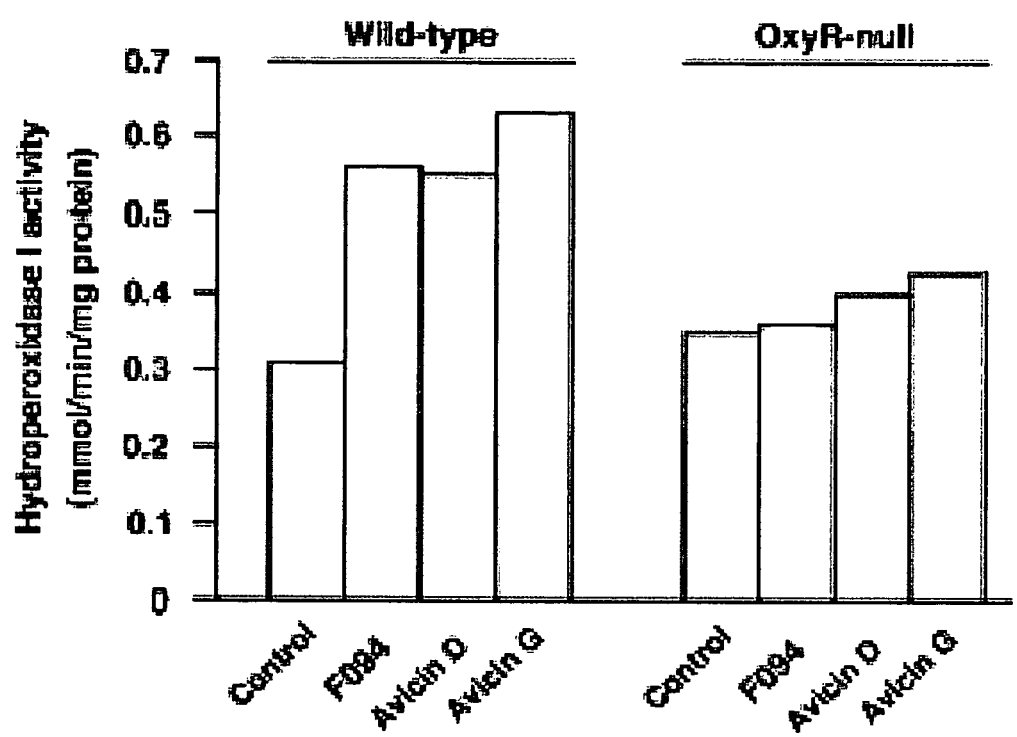
FIG. 2 is a bar graph showing hydroperoxidase I activity in wild type and OxyR null *E. coli* strains in the presence and absence of avicins.

As shown in FIG. 2, F094, avicin D, and avicin G doubled HPI activity in wild-type cells, whereas no increase in activity was seen in OxyR-null cells. That avicin G was as potent an inducer of HPI as F094 and avicin D, even though its in vitro transcriptional activity was lower (FIG. 1), suggests that avicins may have additional direct effects on protein activity.

Example 2

Avicins Couple their Outer Monoterpene to OxyR

To identify the nature of the modification, the structure of avicin-modified OxyR was analyzed by ESI/MS (FIG. 3) and MALDI-TOF/MS (Table 1). In FIG. 3A, the structures of avicins D and G show the presence of two monoterpenoid (MT) units (designated MT inner and MT outer), each of which contains an α,β-unsaturated carbonyl group. A third reactive carbonyl group is linked to an oxyester present on C28. Structures I-III show the fragments that would be adducted to a Cys thiol within OxyR by transesterification (oxyester→thioester). In FIG. 3A, structures I-III show the theoretical fragmentation products that would result from scission of avicin fragments thioester-linked to OxyR. To identify the avicin-derived OxyR adduct, we analyzed by ESI/MS the low-molecular-weight products [<500 atomic mass units (amu)] of tryptic digests of OxyR modified by avicin G or D or F409.

As shown in FIG. 3B, the major fragments recovered exhibited masses of 168.1 amu (avicin G) or 188.1 amu (avicin D or F409). Analysis by MALDI-TOF of tryptic digests of avicin-modified OxyR indicated a mass shift of 168.1 amu for the adducts derived from avicins G and D and F409 (Table 1).

TABLE 1

MALD1-TOF/MS of avicin-modified OxyR

| | | | | m/z | |
| --- | --- | --- | --- | --- | --- |
| Residues | Sequence | Cysteine | Modification | Expected | Detected |
| 191-201 | LLMLEDGHCLR | C199 | Control | 1,299.6 | 1,299.86 (5) |
| | | | F094 | 1,299.6 | 1,295.54 (9) |
| | | | | 1,487.6 | 1,436.72 (100) |
| | | | Avicin D | 1,299.6 | 1,295.82 (15) |
| | | | | 1,487.6 | 1,463.96 |
| | | | Avicin G | 1,299.6 | ND |
| | | | | 1,467.6 | 1,463.76 (63) |

Each spectrum illustrates a range of amu of 0-500. The mass of all peaks of intensity ≥20% of the maximum intensity is indicated. Note that an identical mass of 168.1 amu for the adduct derived from avicin G (R-group=H) or avicin D (R-group=OH), as determined by MALDI-TOF/MS, suggests the possible loss of a water molecule (or laser-induced changes during MALDI-TOF/MS). Taken together, these observations rule out the involvement of structures II and III and indicate that structure I is coupled to OxyR (FIG. 3). Michael acceptor sites are apparently not involved in the modification, but rather the reactive (electrophilic) carbonyl group of the outer monoterpene side chain (structure I) subserves transesterification (oxyester→thioester) of OxyR cysteine thiol. Mild alkaline hydrolysis also results in cleavage of avicins that yields structure I (Jayatilake, G. S., et al. (2003) J. Nat. Prod. 66, 779-783), which emphasizes the relative liability of the oxyester linkage that incorporates structure I within avicins.

Modification of OxyR Cys-199 is necessary for transcriptional activation by redox-active molecules, but Cys-208 or -180 may also influence activity (Kim, S. O., et al. (2002) Cell 109, 383-396). MALDI-TOF/MS allowed us to identify the avicin-modified cysteine residue. After tryptic digests of avicin-treated OxyR, all of the expected peptides (mass>500) were detected. The avicin-modified cysteine containing peptides are listed in Table 1. No avicin-modified peptides contained Cys residues other than Cys-199. FIG. 4A shows the probable reaction scheme that results in a thioester bond between Cys-199 of OxyR and the outer monoterpene of the avicin molecule.

To gain further insight into the structural basis of the interaction between OxyR and avicins, we examined the docking of avicin D to OxyR with molecular modeling (SYBYL; Tripos Associates, St. Louis) (FIG. 4B). Connolly surface rendering (Connolly, M. L. (1983) *Science* 221, 709-713) of the crystal structure of the reduced form of OxyR (PDB IDcode 1169) reveals that Cys-199 is situated in a hydrophilic pocket of ≈20 Å diameter at the surface of OxyR, which we have shown previously accommodates GSSG and GSNO (Kim, S. O., et al. (2002) *Cell* 109, 383-396, Hess, D. T., et al. (2005) *Nat. Rev. Mol. Cell. Biol.* 6, 150-166). Docking and energy minimization (Rarey, M., et al. (1996) *J. Mol. Biol.* 261, 470-489) of OxyR and avicin D result in close apposition (3.36 Å) of Cys-199 thiol in OxyR and the reactive carbonyl in the outer monoterpene side chain of avicin D, which would subserve transesterification.

The thiol of Cys-199 is spaced 2.9 Å from the outer oxygen atom (I) that links the outer monoterpenoid unit, 3.75 Å from the R-group oxygen (II) and 4.44 Å from the carbonyl group oxygen (III). (FIG. 4E). Cleavage of avicin D, coupled to thioesterification, leaves the outer monoterpenoid unit of avicin bound to OxyR. Oxygen atoms within avicin D are shown in space-filling representations with conventional coloring (sulfur, yellow; oxygen, red). Other OxyR groups are shown as green lines, and other avicin D groups are shown in orange in 4B, 4C, and 4E and in conventional coloring in 4D.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

We claim:

1. A composition comprising thioesterification agent with the following formula:

wherein $R_1$ represents a chemical moiety selected from the group consisting of hydrogen, substituted aryl, unsubstituted aryl, substituted alkenyl, unsubstituted alkenyl, substituted alkyl, unsubstituted alkyl, substituted alkoxy, and unsubstituted alkoxy, wherein $R_2$ represents a chemical moiety selected from the group consisting of hydrogen, hydroxyl, C1-C5 alkyl, C1-C5 alkylene, C1-C5 alkyl carbonyl, a sugar and a monoterpene group and wherein $R_3$ represents a chemical moiety selected from the group consisting of hydrogen, hydroxyl, C1-C5 alkyl, C1-C5 alkylene, C1-C5 alkyl carbonyl, a sugar and a monoterpene group, and wherein the thioesterification agent is not an avicin with the following formula:

wherein R5 and R6 are selected from the group consisting of hydrogen, C1-C5 alkyl, and an oligosaccharide; wherein R7 is selected from the group consisting of hydrogen, hydroxyl, C1-C5 alkyl, C1-C5 alkylene, C1-C5 alkyl carbonyl, a sugar, and a monoterpene group, and wherein the avicin formula optionally further comprises R4, wherein R4 is selected from the group consisting of hydroxyl, C1-C5 alkyl, C1-C5 alkylene, C1-C5 alkyl carbonyl, a sugar, C1-C5 alkyl ester, and a monoterpene group and R4 is attached to the triterpene moiety or the monoterpene moiety.

2. The agent of claim 1, wherein $R_3$ represents hydrogen.

3. The composition of claim 1, further comprising a targeting agent bound to the thioesterification agent at any site on the thioesterification agent.

4. The composition of claim 3, wherein the targeting agent is selected from the group consisting of NMDA antagonists, neurological agents, anti-artherosclerotic agents, antibiotics, anti-inflammatory agents, and anti-cancer agents, wherein the anti-cancer agent is selected from the group consisting of mitomycin C, mitozolamide, PCNU, taxol, vinblastine sulfate, camptothecin, doxorubicin, pyrazoloacridine, mitoxantrone, 5-fluorouracil, 5-azacytidine, methotrexate, 2'deoxy-5-fluorouridine, ara-C, and pyrazoloimidazole.

5. The composition of claim 3, wherein the targeting agent is a promoter region.

6. The composition of claim 3, wherein the targeting agent is an antibody.

7. The composition of claim 3, wherein the thioesterification agent reversibly modifies a signaling protein by means of a thioester bond to a cysteine residue on the signaling protein and wherein the targeting agent is a small molecule selected from the group consisting of NMDA antagonists, neurological agents, anti-artherosclerotic agents, antibiotics, anti-inflammatory agents, and anti-cancer agents, wherein the anti-cancer agent is selected from the group consisting of mitomycin C, mitozolamide, PCNU, taxol, vinblastine sulfate, camptothecin, doxorubicin, pyrazoloacridine, mitoxantrone, 5-fluorouracil, 5-azacytidine, methotrexate, 2'deoxy-5-fluorouridine, ara-C, and pyrazoloimidazole.

8. The composition of claim 7, wherein the signaling protein is a bacterial protein.

9. The composition of claim 8, wherein the bacterial protein is OxyR.

10. The composition of claim 7, wherein the NMDA receptor antagonist is selected from the group consisting of amantadine, rimantadine, memantine, ketamine, and glutamate.

11. The composition of claim 7, wherein the neurological agent is selected from the group consisting of bupropion, citalopram, clomipramine, desipramine, doxepin, scitalopram, fluoxetine, imipramine, mirtazapine, nortriptyline, phenelzine, sertraline, trancypromine, trazodone, venlafaxine, amantadine, benztropine, bromocriptine, entacapone, levodopa/carbidopa, pramipexole, ropinirole, selegiline, trihexyphenidyl, aripiprazole, chlorpromazine, clozapine, fluphenazine, haloperidol, olanzapine, perphenazine, quetapine, risperidone, thioridazine, thiothixene, trifluoperazine and ziprasidone.

12. The composition of claim 7, wherein the anti-artherosclerotic agent is selected from the group consisting of atorvastatin, cerivastatin, fluvastatin, lovastatin, pravastatin, simvastatin, rosuvastatin clofibrate, gemfibrozil, and fenofibrate.

13. The composition of claim 7, wherein the antibiotic is selected from the group consisting of mitomycin C, actinomycin D, rifamycin B, streptomycin A, tetracyclines, chloramphenicol/chloromycetin, cycloheximide, erythromycin, puromycin, neomycin, penicillin, phenethicillin, ampicillin, carbenicillin, cephalosporin C, vancomycin, gramicidin A, valinomycin, nonactin, polymyxin, colistin, bacitracin, and subtilin.

14. The composition of claim 7, wherein the anti-inflammatory agent is selected from the group consisting of diclofenac, etodolac, flurbiprofen, ibuprofen, indomethacin, ketoprofen, ketorolac, meclofenamate, nabumetone, naproxen, oxaprozin, piroxicam, rofecoxib, sulindac, tolmetin, and valdecoxib.

15. A method for treating a redox state associated pathology in a subject in need thereof comprising the steps of administering to the subject a therapeutic amount of a thioesterification agent, wherein the thioesterification agent is a composition selected from any one of claim 1-3, 4-6, 7-9 or 10-14.

16. The method of claim 15, wherein the subject is a mammal.

17. The method of claim 16, wherein the mammal is a human.

18. The method of claim 15, wherein the redox state associated pathology is selected from the group consisting of inflammation, artherosclerosis, neurological disorder, bacterial infection, and cancer, wherein said cancer is amenable to the anti-cancer effect of said composition.

19. A method of modifying the activity of a signaling protein in a cell comprising administering to the cell the composition of claim 7.

20. The method of claim 19, wherein the signaling protein is OxyR.

21. The method of claim 19, wherein the cell is a bacterial cell.

22. The method of claim 21, wherein the bacteria is *E. coli*.

23. The method of claim 19, wherein the signaling protein is Nrf2.

24. The method of claim 19, wherein the cell is a mammalian cell.

25. The method of claim 24, wherein the mammalian cell is a human cell.

26. A kit comprising in one or more containers, the composition of claim 7.

27. A composition comprising thioesterification agent with the following formula:

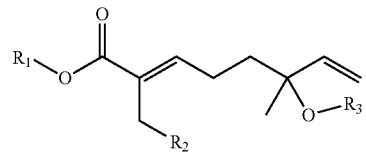

wherein $R_1$ represents a chemical moiety selected from the group consisting of hydrogen, substituted aryl, unsubstituted aryl, substituted alkenyl, unsubstituted alkenyl, unsubstituted alkyl, substituted alkoxy, and unsubstituted alkoxy, wherein $R_2$ represents a chemical moiety selected from the group consisting of hydrogen, hydrorxyl, C1-C5 alkyl, C1-C5 alkylene, C1-C5 alkyl carbonyl, a sugar and a monoterpene group and wherein $R_3$ represents a chemical moiety selected from the group consisting of hydrogen, hydroxyl, C1-C5 alkyl, C1-C5 alkylene, C1-C5 alkyl carbonyl, a sugar and a monoterpene group, and wherein the thioesterification agent is not an avicin with the following formula:

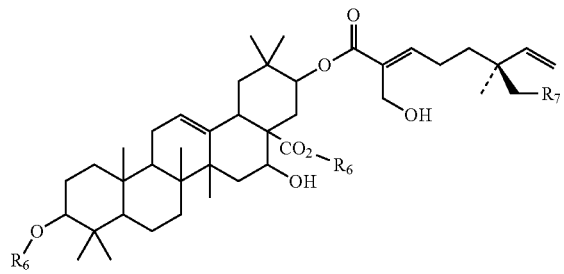

wherein R5 and R6 are selected from the group consisting of hydrogen, C1-C5 alkyl, and an oligosaccharide; wherein R7 I selected form the group consisting of hydrogen, hydroxyl, C1-C5 alkyl, C1-C5 alkylene, C1-C5 alkyl carbonyl, a sugar, and a monoterpene group, and wherein the avicin formula optionally further comprises R4, wherein R4 is selected from the group consisting of hydroxyl, C1-C5 alkyl, C1-C5 alkylene, C1-C5 alkyl carbonyl, a sugar, C1-C5 alkyl ester, and a monoterpene group and R4 is attached to the triterpene moiety or the monoterpene moiety.

* * * * *